United States Patent [19]

Feldman et al.

[11] 3,963,354

[45] June 15, 1976

[54] INSPECTION OF MASKS AND WAFERS BY IMAGE DISSECTION

[75] Inventors: Martin Feldman, Murray Hill; Donald Lawrence White, Bernardsville, both of N.J.

[73] Assignee: Bell Telephone Laboratories, Incorporated, Murray Hill, N.J.

[22] Filed: May 5, 1975

[21] Appl. No.: 574,617

[52] U.S. Cl. .............................. 356/168; 250/562; 250/572; 356/237; 356/239
[51] Int. Cl.² ................ G01B 11/24; G01N 21/32
[58] Field of Search ................ 356/237, 239, 168; 250/562, 563, 572

[56] References Cited
OTHER PUBLICATIONS

"Surface Topography . . . Focused Lasers," Munro et al., Proceedings of Electro-Optics Systems Design Conference, May 18, 1971, pp. 311–317.

"An Automated Inspection System . . . Replicated Patterns," Sittig et al., Proceedings of the Kodak Microelectronics Seminar, Oct. 29–30, 1973, pp. 49–52.

Primary Examiner—Vincent P. McGraw
Attorney, Agent, or Firm—L. C. Canepa

[57] ABSTRACT

In an automated inspection procedure, corresponding elements from all the patterns lying along a row of a replicated-pattern mask or wafer are successively imaged onto a storage medium in an interleaved way. At the completion of an inspection cycle, sets of corresponding elements from all the patterns in the row are respectively arrayed in the storage medium in a side-by-side fashion.

33 Claims, 12 Drawing Figures

INSPECTION OF MASKS AND WAFERS BY IMAGE DISSECTION

BACKGROUND OF THE INVENTION

This invention relates to automated pattern inspection techniques and, more particularly, to the automatic inspection of microminiature masks and wafers that have multiply replicated patterns thereon.

Defects in the masks used in lithographic processes for fabricating microminiature components such as silicon integrated circuits can seriously affect the yield achieved in the manufacture of such components. As the size of these components decreases and as their complexity increases, the problem of inspecting the masks and the components themselves to assure adequate quality becomes increasingly difficult. Visual inspection by an operator of a mask or wafer having multiply replicated microminiature patterns is a time consuming, tedious and often inadequate procedure. As a result, considerable effort has been directed at developing automated inspection systems. In one such known system, patterns on adjacent chips of a mask structure are automatically compared by optically scanning corresponding parts of two adjacent patterns and subtracting the two resulting output signals to obtain an indication of any differences between the two compared parts. Such a two-chip-comparison system is described on pages 49-52 of the *Proceedings of the Microelectronics Seminar* (Interface '73), Oct. 29-30, 1973, Atlanta, Ga., sponsored by the Eastman Kodak Company.

In many instances of practical importance, gradual geometric changes may occur from pattern to pattern across the face of a mask or component wafer. Such changes arise, for example, from cumulative misalignments or from gradual thickness variations from pattern to pattern. Such gradual changes may accumulate to such a gross extent that the patterns at, say, opposite ends of a row of patterns will differ so significantly from each other as not to be acceptable. On the other hand, gradual acceptable changes may occur from pattern to pattern along a row of patterns. If a defect is defined as a unique occurrence in a pattern, an inspection scheme that identifies such minor gradual changes as defects would provide false error indications.

A simple two-chip-comparison inspection may fail to detect gross cumulative changes. Also, such an inspection procedure may fail to identify gradual acceptable changes and, as a result, falsely characterize such changes as defects.

Thus, the need has arisen for an automated inspection technique that provides a microscopic examination of individual patterns while at the same time providing an overall representation of multiple compared patterns so that changes that occur across the face of a mask or wafer may be properly characterized.

SUMMARY OF THE INVENTION

An object of the present invention is the automatic inspection of replicated microminiature patterns.

More specifically, an object of this invention is a system and a method for the automatic inspection of replicated mask and wafer patterns by providing an output representation indicative of multiple compared patterns.

Briefly, these and other objects of the present invention are realized in a specific illustrative embodiment thereof in which corresponding elements from all the patterns lying along a row of a replicated-pattern mask or wafer are successively imaged onto a storage medium in an interleaved way. At the completion of an inspection cycle, sets of corresponding elements from all the patterns are respectively arrayed in the storage medium in a side-by-side fashion. In this way individual patterns are microscopically inspected while at the same time elements from multiple patterns are examined to provide a global comparison of patterns across the entire extent of a mask or wafer.

BRIEF DESCRIPTION OF THE DRAWINGS

A complete understanding of the present invention and of the above and other objects may be gained from a consideration of the following detailed description presented hereinbelow in connection with the accompanying drawing in which:

FIG. 9 is an enlargement of a filter plate included in the FIG. 8 system;

DETAILED DESCRIPTION

Figure 1:
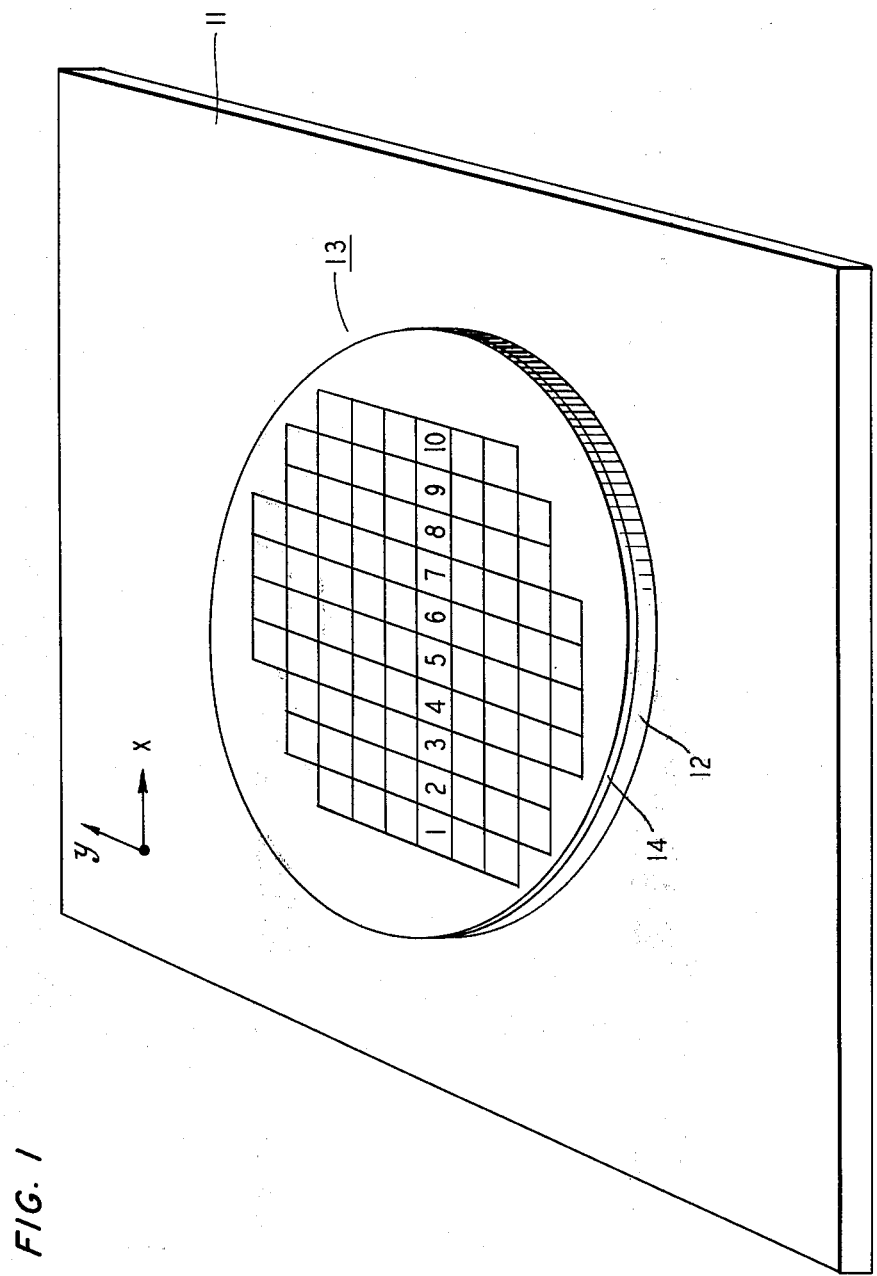
FIG. 1 is a diagrammatic representation of a multiple-pattern mask or wafer mounted on a movable x-y table.

A replicated-pattern structure of the type to be inspected by a system made in accordance with the present invention is shown in FIG. 1. The structure is intended to represent either a mask or a wafer that is mounted on a conventional motor-driven table 11 that is mechanically movable with high precision in both the x and y directions.

Assume, for example, that the structure 13 mounted on the table 11 of FIG. 1 is a mask of the type to be used in fabricating integrated circuits. One such illustrative mask known in the art comprises a substrate 12 made of glass having a layer 14 of an optically opaque material such as chromium deposited thereon. By selectively etching, milling or otherwise removing specified portions of the chrome layer 14, multiple microminiature patterns comprising transparent and opaque regions can be formed in the depicted structure. These transparent and opaque regions are not actually shown in FIG. 1 but their nature and arrangement are well known in the art.

In many cases the multiple patterns formed in the mask structure of FIG. 1 are intended ideally to be exact or nearly replicas of each other. Each pattern is assumed to be contained within one of the squares shown in FIG. 1 arranged in an array of rows and columns. The lines forming the array do not actually exist in the mask structure but are included in FIG. 1 to assist in conceptualizing the placement of the respective multiple patterns. Illustratively, each pattern of transparent and opaque regions formed in the FIG. 1 structure measures about 5 millimeters by 5 millimeters. And, as shown in FIG. 1, as many as 10 such patterns occur along rows and columns of the depicted array.

As will be described in detail later hereinbelow, inspection of a mask structure that includes multiple patterns each comprising transparent and opaque regions is carried out in accordance with the present invention by directing light at the bottom surface of the structure. The portion of the incident light that is transmitted through the transparent regions of the structure is subsequently processed and detected to provide an indication of the quality of the mask.

Alternatively, the structure 13 mounted on the table 11 of FIG. 1 is a wafer comprising multiple chips each of which has one or more microminiature devices or circuits formed therein. In many cases the patterns formed in the respective chips are intended to be exact or nearly exact replicas of each other. In one such specific structure the substrate 12 is, for example, made of silicon and the layer 14 comprises silicon dioxide. By selectively removing portions of the layer 14 and diffusing or implanting impurities through the openings provided thereby, the constituents of conventional electronic components are formed. In turn connections therebetween are made in a manner known in the art by utilizing suitable patterned single or plural metallization levels.

As will be described in detail later hereinbelow, inspection of a wafer structure that includes multiple patterns is carried out in accordance with the present invention by directing light at the top surface of the structure. The incident light is selectively reflected from the wafer contours and is subsequently processed to provide an indication of wafer quality.

Figure 2:
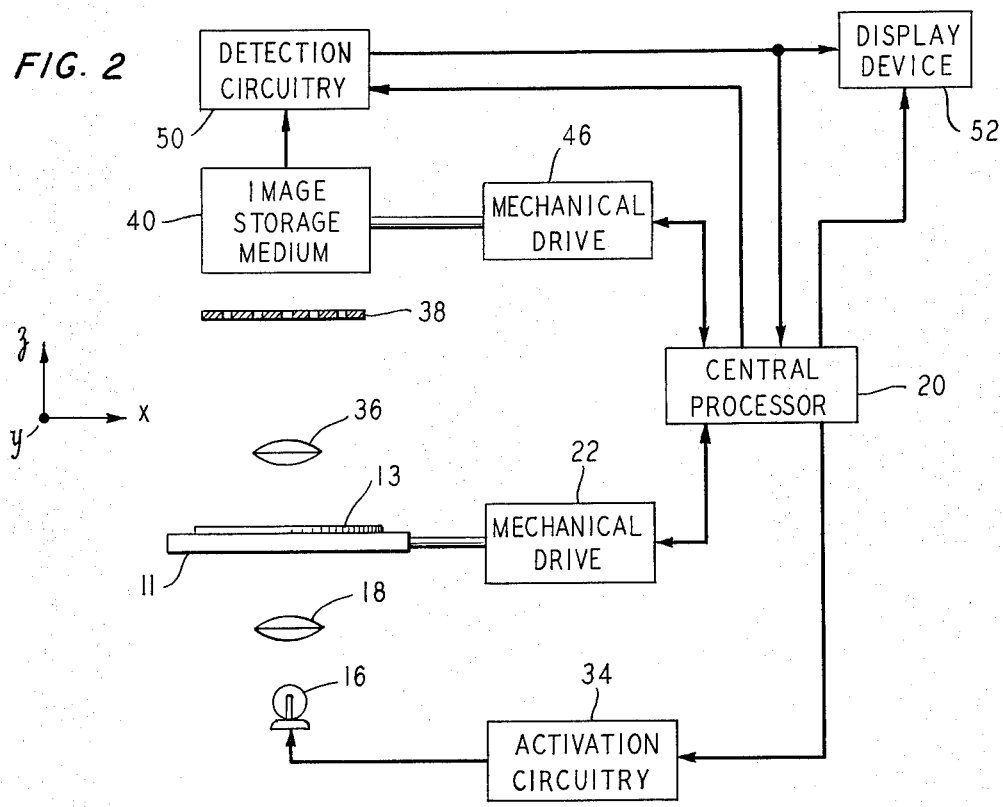
FIG. 2 shows a specific illustrative mask inspection system made in accordance with the principles of the present invention.

A specific illustrative mask inspection system made in accordance with the principles of the present invention is schematically shown in FIG. 2. The x-y table 11 of FIG. 1 carrying a mask structure 13 is included in FIG. 2. Light to be transmitted through transparent regions of the mask 13 is provided by a conventional flash-lamp 16 whose radiant output is directed by lens 18 to fall on an area of the mask that corresponds to a single one of the square patterns represented in FIG. 1.

To permit light from the lamp 16 of FIG. 2 to impinge upon the bottom surface of the mask 13, the table 11 may be made of a suitable light transmissive material such as glass. Alternatively, the mask 13 may be mounted directly above an aperture (not shown) in the table 11.

During a mask inspection cycle, control signals from central processor 20 are applied to x-y mechanical drive 22 to position the table 11 in a location to begin an x-direction scan. Assume, for example, that it is desired to inspect the row of 10 patterns designated 1 through 10 in FIG. 1. In that case the table 11 of FIG. 2 is moved to the far right by the drive 22 to an initial position wherein pattern No. 1 of the mask structure 13 is located directly above the lens 18. The processor 20 is signaled by a conventional code plate or interferometer (not shown) associated with the table 11 that the table is located in position to start a scan cycle. In response thereto a start signal is applied by the processor 20 to activation circuitry 34 to momentarily energize the flash-lamp 16. As a result, pattern No. 1 is illuminated and an image thereof formed by lens 36 is projected toward an apertured plate 38 that comprises slots in an opaque member. In this way, as described in detail below, spaced-apart columns in pattern No. 1 are imaged onto the face of a conventional image storage medium 40. The medium 40 comprises, for example, a square-faced vidicon capable of resolving an array of 500 elements in each of the x and y directions.

By way of example, it is noted that the medium 40 may advantageously comprise a linear charge-coupled imaging device. This device comprises a silicon chip along whose length and width are multiple light-sensitive elements that measure the light transmitted through herein-specified sites of the mask 13. The absorption of light by a single light-sensitive element causes a packet of electrons to accumulate at the element. Each packet of accumulated charge is proportional to the intensity of light transmitted through a signle elemental area of the mask.

On the surface of the silicon chip of such a charge-coupled device are electrodes that permit the periodic transfer of these charge packets in sequence to an output electrode. The current resulting from the arrival of the charge packets at the output electrode therefore furnishes an analog measure of the light incident on an elemental area of the device. (For more details on the structure and operation of charge-coupled imaging devices, see "Charge-Coupling Technology Leads to Compact Video Cameras", *Bell Laboratories Record*, pages 266–271, Oct. 1973.)

Figure 4:
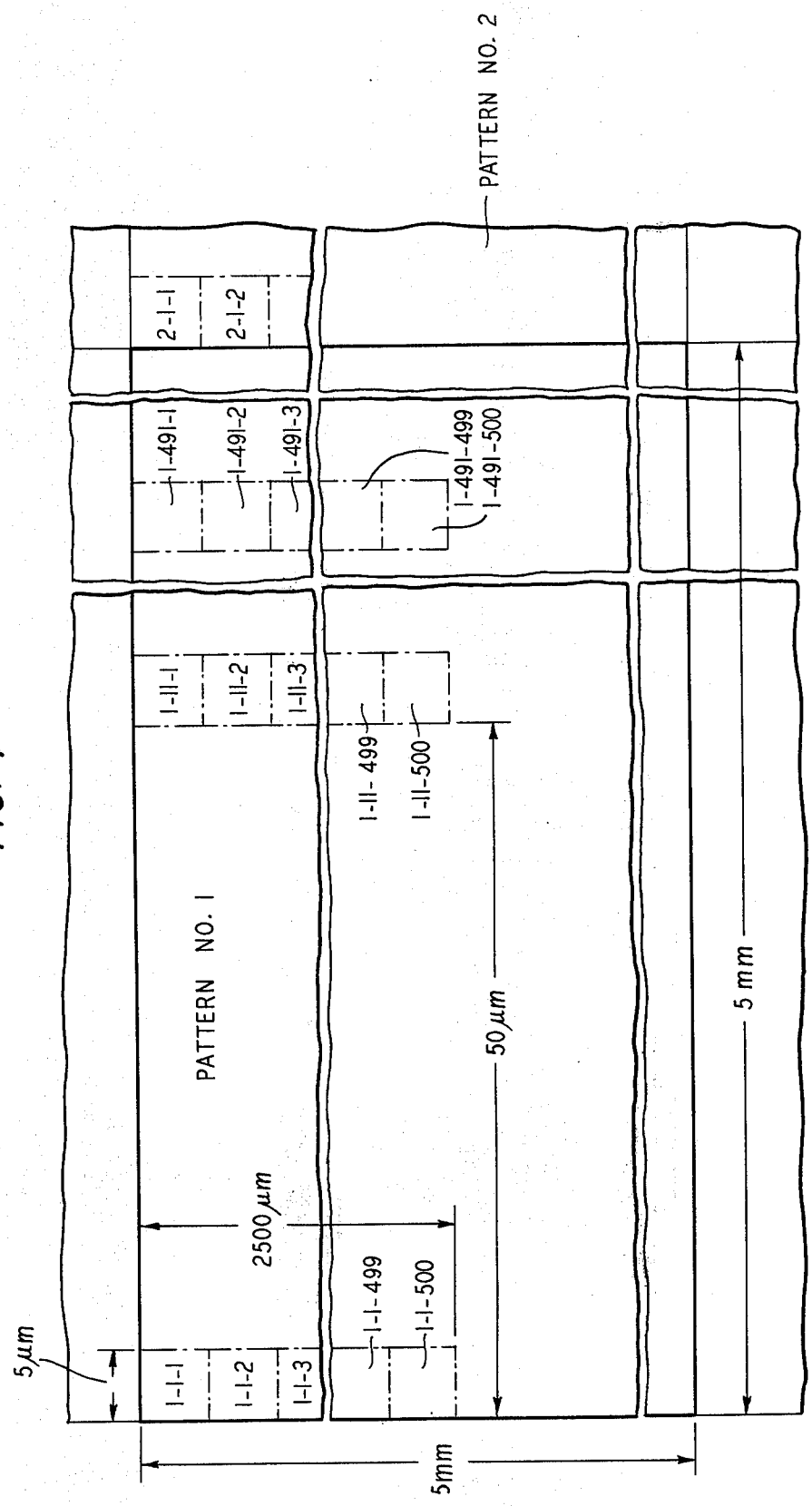
FIG. 4 represents a portion of a mask or wafer pattern to be inspected.

FIG. 4 is an enlarged view of pattern No. 1 of FIG. 1. (Again, to avoid unduly cluttering the drawing, a conventional mask pattern composed of transparent and opaque regions is not actually depicted in FIG. 4. Such patterns are well known in the art and may take a variety of forms.) The individual dashed-line boxes in FIG. 4 represent approximately the basic constituent areas of the pattern that are imaged on the face of the storage medium 40 (FIG. 2) in accordance with the principles of the present invention in response to the aforementioned illumination of pattern No. 1.

To provide a particular example of the mode of operation of applicants' FIG. 2 mask inspection system, it will be helpful to set forth specific illustrative dimensions for the mask pattern represented in FIG. 4. Assume, for example, that pattern No. 1 is one of multiple "identical" patterns each contained in an area 5 millimeters by 5 millimeters (see dimensions marked on FIG. 4). The spaced-apart dashed-line columns of pattern No. 1 each measure 5 micrometers by 2500 micrometers. These columns are spaced at 50-micrometer intervals and there are 50 such columns.

To assist in visualizing the correspondence to be described below between the constituent elements of pattern No. 1 and the image produced on the storage medium 40 of FIG. 2, each of the pattern elements included in the dashed-line columns of FIG. 4 has been assigned a three-integer designation. The first integer signifies the pattern number, the second integer indicates the column position in the pattern and the third integer repesents the row position in the pattern. Thus, the designation 1-1-1 in the upper left-hand element of FIG. 4 indicates that that element is a part of pattern No. 1 and that it is in the first (left-most) column and first (top-most) row of pattern No. 1. Accordingly, the bottom-most element in the first column of pattern No. 1 is designated 1-1-500. The next spaced-apart column of pattern No. 1 that will be initially imaged on the storage medium 40 is actually the eleventh 5-micron-wide column from the left. Accordingly, the top-most and bottom-most elements of that column are designated 1-11-1 and 1-11-500, respectively. A portion of the right-most one of the fifty columns of pattern No. 1 to be imaged initially on the medium 40 is also shown in FIG. 4. The top-most and bottom-most elements of this column are designated 1-491-1 and 1-491-500, respectively.

As noted earlier, the entire area of pattern No. 1 is momentarily illuminated in response to activation of the flash-lamp 16 of FIG. 2. But, due to the action of the apertured plate 38, only spaced-apart columns of pattern No. 1 are imaged onto the face of the medium 40. A specific illustrative depiction of one type of plate suitable for achieving this result is shown in FIG. 5.

Figure 5:
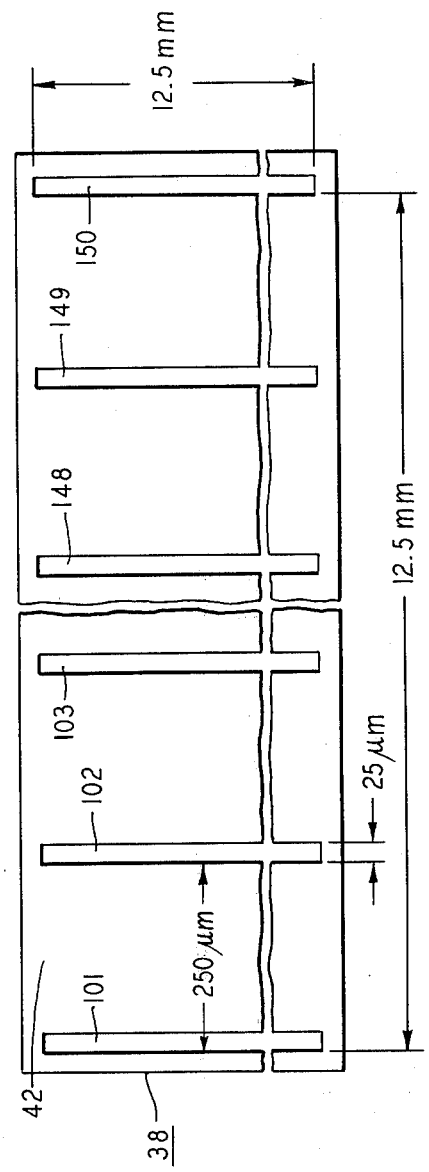
FIG. 5 is an enlargement of an apertured plate included in the systems of FIGS. 2 and 3.

The plate 38 depicted in FIG. 5 includes multiple slots formed in an opaque member 42. In the particular case in which 50 spaced-apart columns of each pattern are to be imaged at a time onto the storage medium 40, the plate 38 includes 50 slots 101, 102, 103, . . . 148, 149, 150. Each such slot is arranged to pass therethrough an image of a correspondingly positioned one of the dashed-line columnar areas represented in FIG. 4. Thus, for example, images of the 500 elements comprising the first dashed-line column shown in FIG. 4 are passed through the slot 101, and the images of the 500 elements comprising the fiftieth column of FIG. 4 are transmitted through slot 150. Images of the 48 other previously described spaced-apart columns of pattern No. 1 are respectively transmitted through the other slots 102, 103, . . . 148, 149, represented in FIG. 5.

An illustrative set of approximate dimensions for the plate 38 is indicated in FIG. 5. In a specific system made in accordance with the principles of the present invention, these dimensions correspond to those set forth above for pattern No. 1. Thus, the respective images of the 500 individual 5-micrometer-by-5-micrometer elements included in each dashed-line column of FIG. 4 are each, for example, expanded to approximately 25 micrometers by 25 micrometers in size as they are transmitted through the associated one of the slots of FIG. 5.

Figure 6:
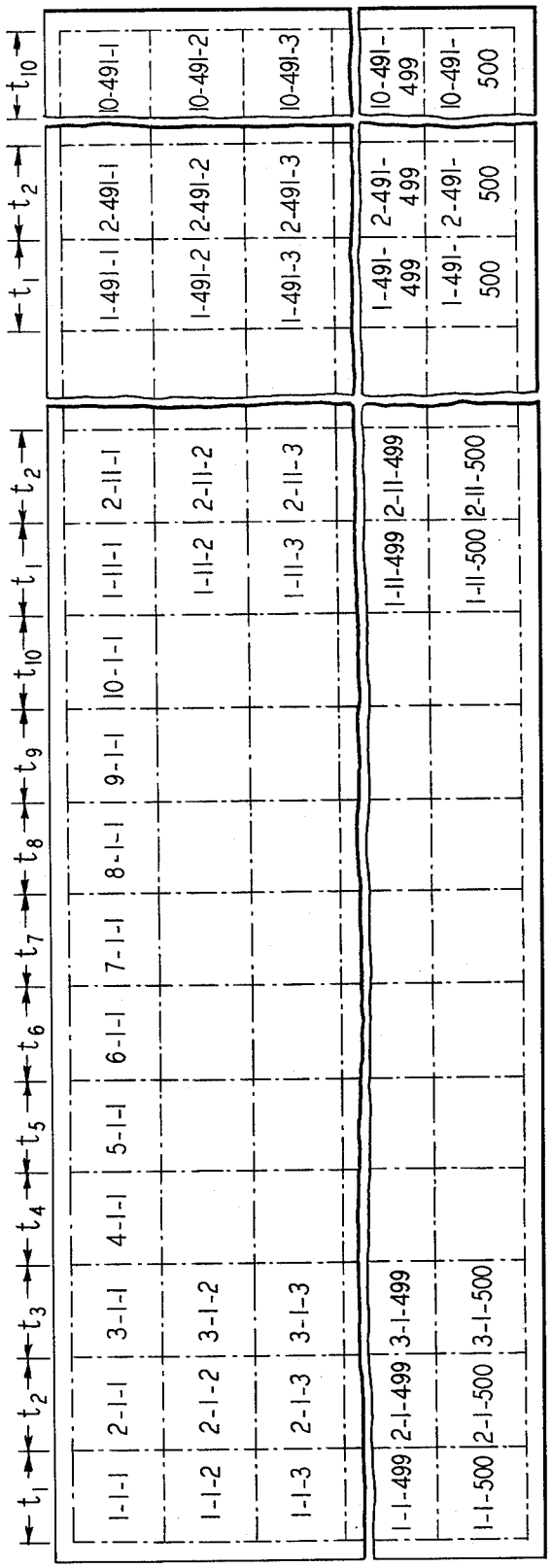
FIGS. 6 and 7 are schematic representations, during successive inspection cycles, of the face of an image storage medium included in the systems of FIGS. 2 and 3.

In response to illumination of pattern No. 1 at time $t_1$, images of the 50 aforespecified spaced-apart columns thereof are transmitted through the plate 38 (FIG. 5) to impinge on the face of the storage medium 40 (FIG. 2). These images are depicted in FIG. 6 which represents the fact of medium 40. The individual image elements of FIg. 6 are identified with the same three-integer designations included in FIG. 4 and respectively correspond therewith.

Moreover, indications are included in FIG. 6 to show at what times the depicted images are impressed on the face of the storage medium 40. As represented in FIG. 6, 50 spaced-apart columnar areas from pattern No. 1 are imaged onto the medium 40 at time $t_1$ which corresponds to the initial momentary period during which pattern No. 1 is illuminated by the lamp 16.

Illustratively, movement of the table 10 of FIG. 2 in the x direction is continuous during the successive momentary illuminations of patterns 1 through 10. Activation of the flash-lamp 16 to illuminate the entire area of pattern No. 2 is controlled by the processor 20 to occur at time $t_2$ when pattern No. 2 is positioned in alignment with the lamp 16 and the lens 18.

Subsequent to illumination of pattern No. 1 at time $t_1$ and before illuminating pattern No. 2 at time $t_2$, the storage medium 40 is stepped to the left in a direction parallel to the x axis. More specifically, the medium 40 is moved to the left a distance equal to the width of one of the dashed-line image elements shown in FIG. 6. This is accomplished by applying appropriate control signals from the processor 20 to a standard mechanical drive or micropositioner 46 (FIG. 2) that is coupled to the medium 40.

As a result of the aforedescribed translation of the storage medium 40, illumination of pattern No. 2 at time $t_2$ will cause 50 spaced-apart columns thereof to be imaged onto the face of the medium 40 at positions that are respectively adjacent the previously described 50 spaced-apart columns of pattern No. 1. This is represented in FIG. 6 wherein, for example, the 500 elements in the first column of pattern No. 2 (numbered 2-1-1 through 2-1-500) are shown respectively adjacent the 500 elements in the first column of pattern No. 1 (1-1-1 through 1-1-500). Further, the 500 elements in each of the 11th and 491st columns of pattern No. 2 are shown respectively adjacent the 500 elements in the 11th and 491st columns of pattern No. 1. These specified columns, as well as 47 other spaced-apart ones from pattern No. 2, are imaged onto the medium 40 at time $t_2$, as indicated in FIG. 6.

Next, between illumination intervals $t_2$ and $t_3$ the storage medium 40 of FIG. 2 is again stepped to the left a distance equal to the width of one image element. Accordingly, momentary illumination of pattern No. 3 at time $t_3$ will cause 50 spaced-apart columns of pattern No. 3 to be imaged onto the face of the medium 40 at positions that are respectively adjacent the above-described 50 spaced-apart columns of pattern No. 2. This is represented in FIG. 6 wherein it is indicated, for example, that at time $t_3$ the first column of pattern No. 3 is imaged directly adjacent the first column of pattern No. 2.

In a similar way, 50 corresponding columns from each of patterns 4 through 10 are subsequently imaged in sequence onto the face of the storage medium 40. These spaced-apart columns from each of patterns 4 through 10 are projected as a group onto the medium 40 during time intervals $t_4$ through $t_{10}$, respectively, as represented in FIG. 6. Thus, after 10 timed flashes of the lamp 16 of FIG. 2, the corresponding 10 left-most columns of patterns 1 through 10 are located in a directly adjacent side-by-side fashion on the face of the image storage medium 40. In addition, the other 49 columns from each of the 10 row patterns are respectively grouped together in sets of 10 in the medium 40.

AT this point in the inspection cycle (i.e., after $t_{10}$) the medium 40 of FIG. 2 is completely exposed. Accordingly, an image array of 500 by 500 elements is stored therein. Readout of the medium 40 then occurs. This is accomplished by conventional detection circuitry 50 controlled by the processor 20. Signals from the circuitry 50 are, for example, applied directly to a display device 52 for visual examination and/or are applied to the processor 20 for semipermanent storage therein and/or for the purpose of performing various signal transformations.

Illustratively, the detection circuitry 50 is controlled to scan 10 row elements at a time of the array stored in the medium 40. Thus, for example, signals representative of the 10 elements designated 1-1-1, 2-1-1 . . . 10-1-1 in FIG. 6 are abstracted serially from the medium 40. These 10 signals are respectively representative of the same elemental area of each of patterns 1 through 10. Ideally, these areas are identical to each other and hence the electrical signals derived therefrom are also identical. The top-most waveform 54 of FIG. 12 indicates such a situation. As shown there, the amplitudes of the signals derived from the areas 1-1-1, 2-1-1, . . . 10-1-1 are constant and equal to each other. Such a waveform can be displayed on the device 52 of FIG. 2 for visual examination by an operator.

Figure 12:
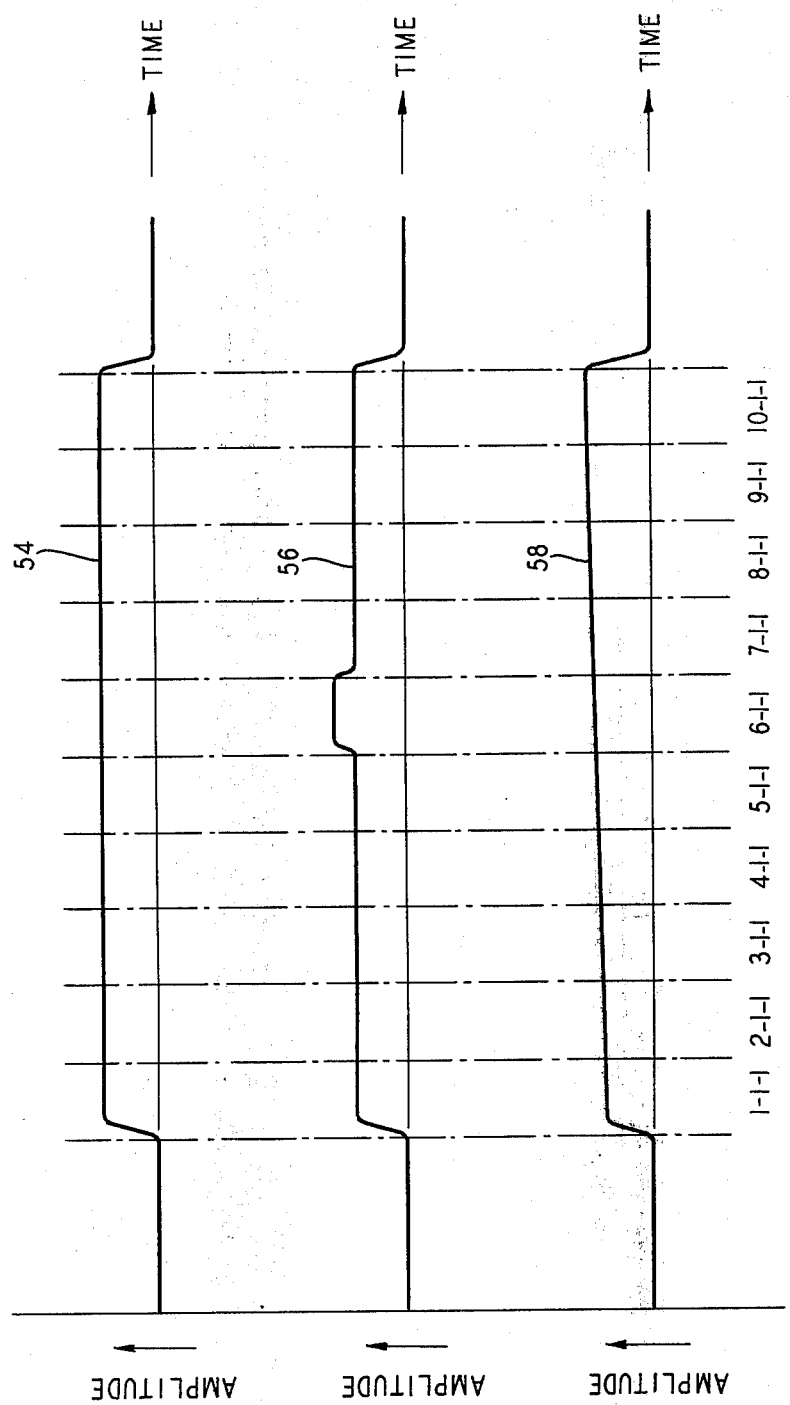
FIG. 12 shows various output waveforms provided by inspection systems made in accordance with the principles of this invention.

A genuine defect in one of the elemental areas 1-1-1, 2-1-1, . . . 10-1-1 is represented by the middle waveform 56 of FIG. 12. A defect in area 6-1-1 is distinctively indicated. This indication arises from the fact that the intensity of light transmitted through the upper left-hand area of pattern No. 6 differs significantly from that transmitted through each of the corresponding areas of patterns 1 through 5 and 7 through 10.

Verification that the signal derived from area 6-1-1 and displayed on the device 52 is a true defect signal can be made (for example, in the processor 20) by comparing the 6-1-1 signal with the average of the signals obtained from areas 5-1-1 and 7-1-1 or with some other weighted average of all the other signals. Or the 10 signals can be processed to determine whether or not the composite representation 56 is monotonic in nature. Or by standard signal processing techniques the signals constituting the waveform 56 can be examined in the processor 20 to verify that the 6-1-1 signal does not closely match at least one of the 5-1-1 and 7-1-1 signals.

The bottom-most waveform 58 of FIG. 12 represents the situation wherein gradual monotonic changes take place from pattern to pattern across the face of the inspected mask. As indicated earlier above, such gradual changes may be acceptable. If they are acceptable, the inspection system should not, of course, signal the occurrence of an error. By comparing the signal stemming from say area 7-1-1 with the average of the signals from areas 6-1-1 and 8-1-1, the processor 20 of FIG. 2 would determine that the 7-1-1 signal of the waveform 58 is not indicative of an error. Signal comparisons in the processor 20 between each component signal of the waveform 58 and the average of the adjacent signals serve to correctly characterize the detected signals.

In a simple conventional two-chip-comparison system, the difference between the 7-1-1 and 8-1-1 signals might be falsely classified as arising from a fault. To guard against such a false indication, the threshold of the conventional system could be adjusted to exceed the difference in level between two corresponding points of the 7-1-1 and 8-1-1 signals. But such an adjustment would obviously impair the sensitivity of the inspection process. By contrast, in accordance with the image-dissection technique of the present invention, the threshold setting may be established as the difference between a point of the 7-1-1 signal and the average of corresponding points of the 6-1-1 and 8-1-1 signals. For a waveform of the type designated 58 in FIG. 12, this is a smaller value than the threshold specified above for the conventional two-chip-comparison system. Hence the herein-considered inspection technique is characterized by the capability to detect faults in a more sensitive way and, as indicated earlier above, by a greater immunity to false detection.

In an exactly similar manner, subsequent readout, 10 elements at a time, of the image array represented in FIG. 6 is carried out until the signals derived from all 500 elements in the first row have been displayed and/or processed. Then the other 499 rows of the FIG. 6 array are scanned in sequence in the same way. During scanning of the stored array the table 11 of FIG. 2 is moved by the drive 22 back to its initial location. After readout of the entire 500-element-by-500-element array stored in the medium 40 is complete, the medium 40 is erased (if necessary) and is mechanically returned to its initial location.

Figure 7:
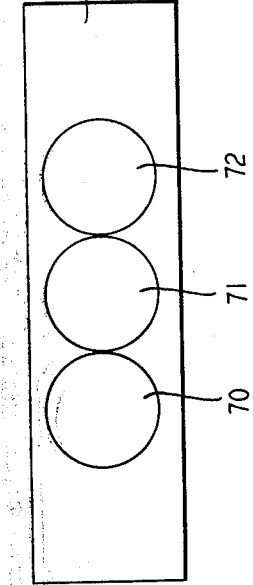

At this point the FIG. 2 system is ready to commence another cycle of operation. During this next cycle the table 11 is again moved in a continuous way in the x direction from right to left. But activation of the flashlamp 16 to illuminate patterns 1 through 10 in succession is controlled to occur in a time-displaced way relative to the first above-described illumination of those patterns. More specifically, pattern No. 1 is not illuminated until the table 11 has moved to the left from its starting point by the width (for example, 5 micrometers) of one of the elemental columns specified above and represented in FIG. 4. As a result of this displacement the 50 spaced-apart columns of pattern No. 1 that are imaged onto the face of the medium 40 are the second, 12th, 22nd, . . . 492nd columns of pattern No. 1. Patterns 2 through 10 are subsequently illuminated in this same offset manner. The resulting 500-element-by-500 element array stored in the medium 40 is represented in FIG. 7. Readout of the medium 40 then takes place in the manner specified above. Thereafter, in eight subsequent similar cycles of operation, the remaining elements in the upper left-hand quarter of each of patterns 1 through 10 are imaged onto the element 40. Next, the elements in the upper right-hand quarter of each of patterns 1 through 10 are inspected in the illustrative manner specified herein. Then the table 11 of FIG. 2 is moved into the plane of the drawing in the y direction (for example, by 2.5 millimeters) to locate the lower half of each of patterns 1 through 10 in position for inspection by the image-dissection technique described above and embodied in the FIG. 2 system.

As mentioned earlier above, the principles of the present invention are also applicable to wafer inspection. In fact, the application of these principles to the inspection of wafers is particularly significant. This is so because of the practical necessity to accommodate a wafer inspection technique to the changes that typically occur in chip geometry across the face of a wafer. These changes arise, for example, from processing variations and from misregistration of different levels during chip fabrication.

Figure 3:
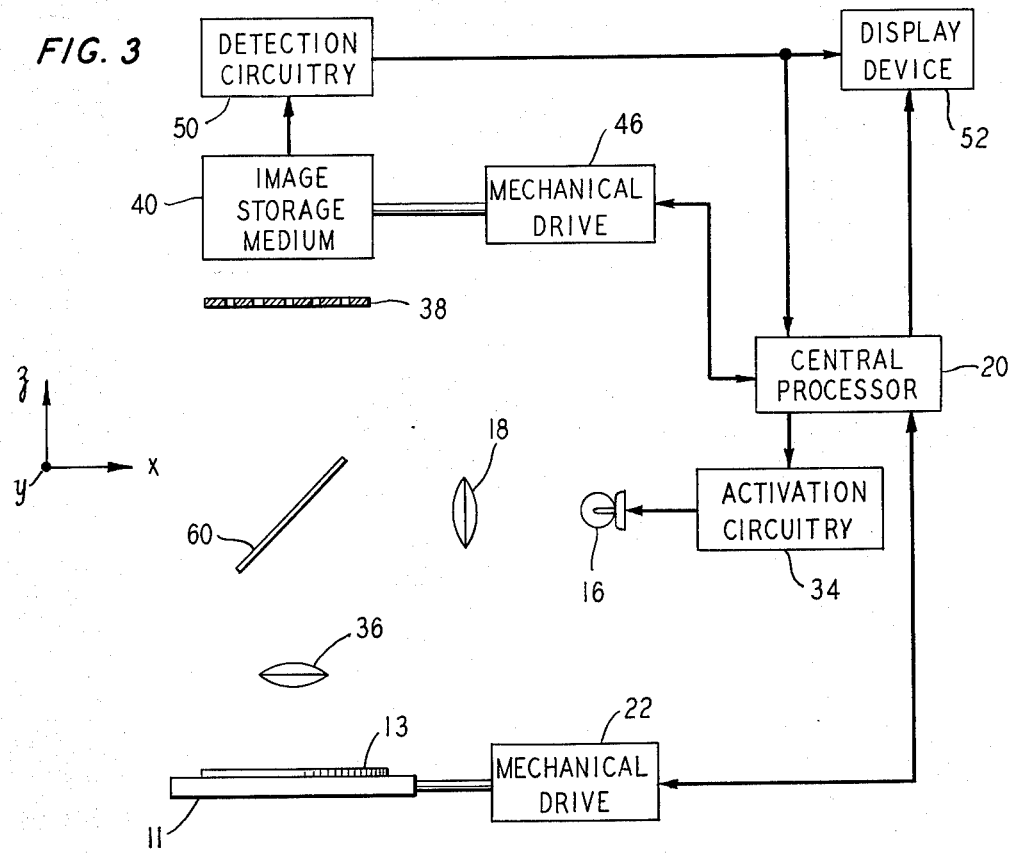
FIG. 3 depicts a specific illustrative wafer inspection system made in accordance with the principles of the present invention.

A specific illustrative wafer inspection system made in accordance with the principles of the present invention is shown in FIG. 3. A number of the components included in FIG. 3 may be identical to previously described units depicted in FIG. 2. These components are identified in FIG. 3 by the same reference numerals employed therefor in FIG. 2.

The wafer inspection system of FIG. 3 involves reflecting light from the top surface of the wafer member 13 carried by the movable table 11. (In FIG. 2 light is transmitted through the transparent portions of the mask member 13.) Accordingly, in FIG. 3 the flashlamp 16 is positioned relative to a conventional beam splitter 60 and lens 36 to direct light onto the top surface of the wafer 13. In turn, light reflected from the surface contours of the wafer is imaged by the lens 36 and transmitted by the beam splitter 60 toward the apertured plate 38. In the same manner specified above in connection with FIG. 2, the plate 38 of FIG. 3 serves to allow only spaced-apart columns of the incident light to impinge upon the face of the image storage medium 40.

The amount of light reflected from an elemental area of a wafer varies as a function of wavelength. Moreover, the amount of light reflected from an area at a particular wavelength varies with, for example, variations in thickness of a metal or an oxide included in the area. Thus, by systematically monitoring the amount of light reflected from a particular area at various wavelengths, significant data concerning the contour and composition of the area is obtained. In turn, conventional processing of such data can give important diagnostic information concerning an inspected wafer.

Figure 8:
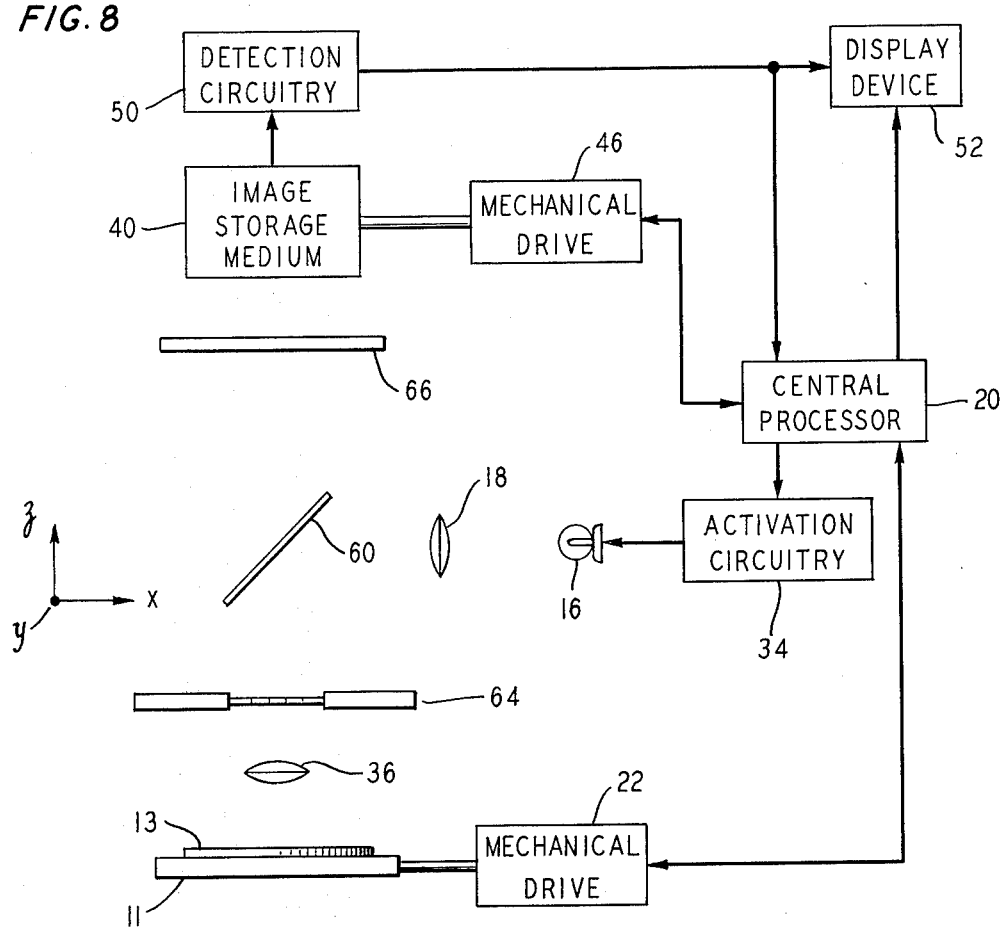
FIG. 8 is a modified version of the wafer inspection system shown in FIG. 3.

A specific illustrative wafer inspection system in which each elemental area of the wafer is in effect optically inspected simultaneously at three different wavelengths is shown in FIG. 8. Previously described components are designated in FIG. 8 with the same reference numerals employed therefor in FIGS. 2 and 3. Additional elements 64 and 66, to be described hereinbelow, are included in FIG. 8.

Light from the lamp 16 of FIG. 8 is directed downward by the beam splitter 60 through the element 64. Illustratively, the element 64 comprises a member supporting three filters. A top schematic view of the filters is shown in FIG. 9. From left to right the three filters 70, 71 and 72 supported by opaque member 73 are selected to pass only red, green and blue light, respectively. Light transmitted through each of the filters is directed by lens 36 (FIG. 8) to impinge in parallel upon a single one at a time of the patterns included in the member 13. Accordingly, as mentioned above, each pattern is in effect inspected in three different colors.

Figure 10:
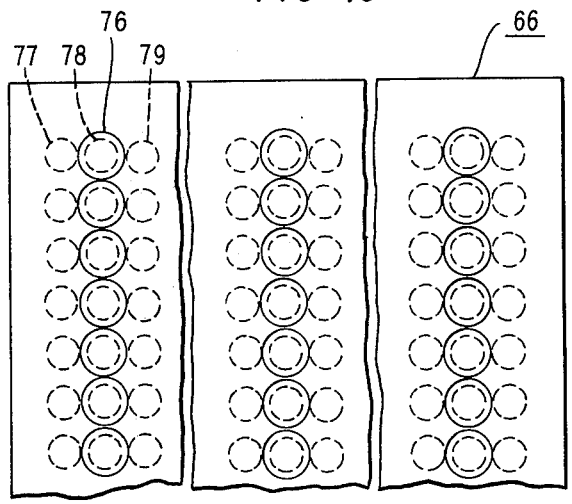
FIGS. 10 and 11 are enlargements of lenslet arrays suitable for inclusion in the FIG. 8 system.

Light reflected from the top surface of the wafer member 13 is directed by the lens 36 to pass through the element 64 and the beam splitter 60 and to image upon the element 66. A top view of one specific illustrative form of the element 66 is shown in FIG. 10. As indicated in FIG. 10, the element 66 comprises, for example, individual columns of conventional miniature lenslets. The spacing between adjacent columns, as well as the width and height of each column, may for example, correspond approxiamtely to the spacing and dimensions of the slots included in the apertured plate 38 of FIG. 3.

Red, green and blue light reflected from each elemental area of a pattern on the wafer 13 of FIG. 8 is directed through a single lenslet in a column of lenslets. In turn, the single lenslet causes three images of the elemental area to be formed on the face of the storage medium 40. Thus, for example, as represented in FIG. 10, red, green and blue light reflected from a single elemental pattern area is directed by lenslet 76 to form blue, green and red images, represented by dashed-line circles 77, 78 and 79, respectively. Each other lenslet in FIG. 10 is indicated to form three distinct images along a line perpendicular to the lenslet column. Accordingly, for inspection of a wafer in the particular manner described earlier above, the storage medium 40 positioned behind the element 66 of FIG. 10 is selected to have the capacity to image 1500 separate elements along its horizontal dimension and 500 elements along its vertical dimension.

Figure 11:
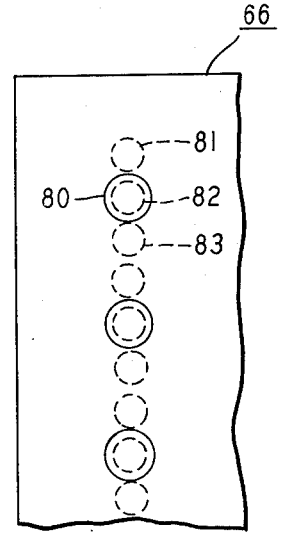

Alternatively, the three images derived from each elemental pattern area of the wafer inspection system of FIG. 8 may be arranged to occur on the face of the storage medium 40 parallel to the lenslet columns. This is accomplished, for example, by arranging the individual lenslets in each column as shown in FIG. 11. Illustratively, red, green and blue light from a single elemental area is directed at lenslet 80. In turn, the lenslet 80 forms three images, represented as dashed-line circles 81, 82 and 83 on the face of the medium 40. Hence, in this fashion, the medium 40 is designed to image an array of 500 horizontal elements by 1500 vertical elements.

The technique of image dissection as embodied in the specific illustrative systems described herein is a powerful solution to the problem of inspecting masks and wafers. As indicated above, one major advantage of the technique is its ability to track gradual geometric and color changes across a set of patterns and to distinguish such changes from the abrupt changes caused by defects.

Finally, it is to be understood that the above-described methods and systems are only illustrative of the application of the principles of the present invention. In accordance with these principles, numerous modifications may be devised by those skilled in the art without departing from the spirit and scope of the invention. For example, it is apparent that the filter element 64 of FIG. 8 may be moved to a position between the beam splitter 60 and the element 66. In that embodiment the wafer 13 is illuminated by the unfiltered output of the lamp 16 and color separation is performed only after the incident light is reflected from the surface of the wafer 13.

What is claimed is:

1. An image dissection system for inspecting a member that contains multiple patterns that are nominally identical to each other, said system comprising
    means for momentarily illuminating one pattern at a time of the multiple patterns,
    an image storage medium,
    means responsive to light emanating from the illuminated pattern for impressing images of only spaced-apart portions of said pattern onto said image storage medium,
    and means for positioning the images from successive patterns in an interleaved side-by-side way in said image storage medium.

2. In an inspection system, means for sequentially and momentarily illuminating successive adjacent pattern areas of a member to be inspected,
    means for projecting an image of an illuminated pattern area toward said image storage means,
    means interposed between said projecting means and said image storage means for transmitting to said image storage means only spaced-apart portions of the image of an illuminated pattern area,
    and means for translating said image storage means between successive illuminations of adjacent pattern areas so that corresponding portions of successive pattern areas are imaged on said image storage means in a side-by-side fashion.

3. A combination as in claim 2 wherein said successive adjacent pattern areas comprise nominally identical transparent and opaque portions of a mask to be inspected, and wherein said illuminating means includes a source for transmitting light through the transparent portions of said mask toward said image storage means.

4. A combination as in claim 3 wherein said transmitting means comprises an opaque plate having spaced-apart slots through which the spaced-apart portions of the image of an illuminated mask pattern area are respectively transmitted to said image storage means.

5. A combination as in claim 4 wherein said illuminating means further includes a central processor and activation circuitry responsive to timing signals from said processor for controlling the energization of said source.

6. A combination as in claim 5 wherein said illuminating means further includes an x-y movable table on which said mask is supported, and a mechanical drive coupled to said table and responsive to signals from said processor for moving said table.

7. A combination as in claim 6 further including means responsive to the images stored in said image storage means for reading out of said storage means in sequence groups of signals each group of which comprises signals respectively representative of corresponding portions of successive mask pattern areas.

8. A combination as in claim 7 wherein said translating means comprises a mechanical drive coupled to said image storage means and responsive to signals from said processor for moving said image storage means.

9. A combination as in claim 2 wherein said successive adjacent pattern areas comprise nominally identical portions of a wafer to be inspected,
and wherein said illuminating means includes a source for directing light at the top surface of said wafer so that light reflected from the top surface of said wafer is directed toward said image storage means.

10. A combination as in claim 9 wherein said transmitting means comprises an opaque plate having spaced-apart slots through which the spaced-apart portions of the image of an illuminated wafer pattern area are respectively transmitted to said image storage means.

11. A combination as in claim 10 wherein said illuminating means further includes a central processor and activation circuitry responsive to timing signals from said processor for controlling the energization of said source.

12. A combination as in claim 11 wherein said illuminating means further includes an x-y movable table on which said wafer is supported, and a mechanical drive coupled to said table and responsive to signals from said processor for moving said table.

13. A combination as in claim 12 further including means responsive to the images stored in said image storage means for reading out of said storage means in sequence groups of signals each group of which comprises signals respectively representative of corresponding portions of successive wafer areas.

14. A combination as in claim 13 wherein said translating means comprises a mechanical drive coupled to said image storage means and responsive to signals from said processor for moving said image storage means.

15. A combination as in claim 9 further including filter means interposed in the path of light reflected from the top surface of said wafer for directing light of only several distinct wavelengths simultaneously toward said transmitting means.

16. A combination as in claim 9 wherein said illuminating means further includes filter means interposed between said source and said wafer to be inspected for directing light of several distinct wavelengths simultaneously onto one at a time of the wafer pattern areas.

17. A combination as in claim 16 wherein said transmitting means comprises an array of lenslets each of which is arranged to be responsive to the several distinct wavelengths reflected from an elemental area of an illuminated wafer pattern area to form in said image storage means several distinct spaced-apart images each representative of the same elemental area.

18. A combination as in claim 17 wherein said illuminating means further includes a central processor and activation circuitry responsive to timing signals from said processor for controlling the energization of said source.

19. A combination as in claim 18 wherein said illuminating means further includes an x-y movable table on which said wafer is supported, and a mechanical drive coupled to said table and responsive to signals from said processor for moving said table.

20. A combination as in claim 19 further including means responsive to the images stored in said image storage means for reading out of said storage means in sequence groups of signals each group of which comprises signals respectively representative of corresponding portions of successive wafer areas.

21. A combination as in claim 20 wherein said translating means comprising a mechanical drive coupled to said image storage means and responsive to signals from said processor for moving said image storage means.

22. An image dissection method for inspecting a member that contains multiple patterns that are nominally identical to each other, said method comprising the steps of
momentarily illuminating one pattern at a time of the multiple patterns,
and impressing images of only spaced-apart portions of successively illuminated patterns onto an image storage medium in an interleaved side-by-side way to position corresponding portions of the patterns adjacent each other in the medium.

23. An inspection method comprising the steps of
sequentially and momentarily illuminating successive adjacent pattern areas of a mask or wafer member to be inspected,
projecting an image of an illuminated pattern area toward an image storage medium,
transmitting to said image storage medium only spaced-apart portions of the image of an illuminated pattern area,
and translating said image storage medium between successive illuminations of adjacent pattern areas so that corresponding portions of successive pattern areas are imaged on said image storage medium in a side-by-side fashion.

24. A method as in claim 23 wherein said successive adjacent pattern areas comprise nominally identical transparent and opaque portions of a mask member to be inspected, and wherein said illuminating step comprises
transmitting light through the transparent portions of said mask member toward said image storage medium.

25. A method as in claim 24 further including the step of reading out of said image storage medium in sequence groups of signals each group of which comprises signals respectively representative of corresponding portions of successive mask member pattern areas.

26. A method as in claim 25 further including the step of processing the signals read out of said image storage medium to determine whether or not any of the signals of a group is indicative of a defect in said mask member.

27. A method as in claim 25 further including the step of displaying each group of signals read out of said image storage medium to provide a visual indication of any defects in said mask member.

28. A method as in claim 23 wherein said successive adjacent pattern areas comprise nominally identical portions of a wafer member to be inspected, and wherein said illuminating step comprises directing light at the top surface of said wafer member so that light reflected from the top surface of said wafer member is directed toward said image storage medium.

29. A method as in claim 28 further including the step of reading out of said image storage medium in sequence groups of signals each group of which comprises signals respectively representative of corresponding portions of successive wafer member pattern areas.

30. A method as in claim 29 further including the step of processing the signals read out of said image storage medium to determine whether or not any of the signals of a group is indicative of a defect in said wafer member.

31. A method as in claim 29 further including the step of displaying each group of signals read out of said image storage medium to provide a visual indication of any defects in said wafer member.

32. A method as in claim 28 wherein said step of directing light at the top surface of said wafer member includes directing light of several specified wavelengths simultaneously onto one at a time of the wafer member pattern areas.

33. A method as in claim 32 wherein the step of transmitting to said image storage medium only spaced-apart portions of the image of an illuminated wafer member pattern area comprises transmitting to said image storage medium the several wavelengths reflected from an elemental area of an illuminated wafer member pattern area to form in said image storage medium several spaced-apart images each representative of the same elemental area.

* * * * *